United States Patent [19]

Liefke

[11] 4,308,011
[45] Dec. 29, 1981

[54] APPARATUS FOR SUPPORTING DENTAL HANDPIECES

[75] Inventor: Johannes Liefke, Bensheim, Fed. Rep. of Germany

[73] Assignee: Siemens Aktiengesellschaft, Berlin & Munich, Fed. Rep. of Germany

[21] Appl. No.: 40,038

[22] Filed: May 17, 1979

[30] Foreign Application Priority Data

May 31, 1978 [DE] Fed. Rep. of Germany ....... 2823858

[51] Int. Cl.³ .................. A61C 19/02; G01R 33/00; G01V 9/04; H01J 40/14
[52] U.S. Cl. .................................. 433/28; 433/27; 324/260; 250/215
[58] Field of Search ............... 433/28, 27; 250/229, 250/221, 215, 227; 248/550; 324/260

[56] References Cited

U.S. PATENT DOCUMENTS

| 2,971,151 | 2/1961 | Mierendorf et al. | 324/260 |
| 3,262,735 | 7/1966 | Thompson | 433/28 |
| 3,541,394 | 1/1969 | Brenneman et al. | 324/260 |
| 3,638,050 | 1/1972 | Harp | 250/215 |
| 3,900,580 | 8/1975 | Baggs | 250/227 |
| 3,984,764 | 10/1976 | Koerner | 324/260 |
| 4,069,587 | 1/1978 | Peralta | 433/27 |
| 4,106,198 | 8/1978 | Childress | 433/28 |
| 4,114,273 | 9/1978 | McGaha | 433/78 |
| 4,119,845 | 10/1978 | Jaskolski et al. | 250/229 |
| 4,186,388 | 1/1980 | Robinson | 250/221 |

Primary Examiner—Gene Mancene
Assistant Examiner—Michael J. Foycik
Attorney, Agent, or Firm—Hill, Van Santen, Steadman, Chiara & Simpson

[57] ABSTRACT

An improved apparatus for storing dental handpieces which includes a support device for each of the handpieces and a switching device for creating a signal when a handpiece is disposed in the supporting devices without contacting the handpiece. In one embodiment, the sensing device utilizes a light barrier which is broken by placing the handpiece in the supporting device and in another embodiment the sensing device utilizes a coil and resonant circuit whose output is changed by the presence of the handpiece.

10 Claims, 4 Drawing Figures

APPARATUS FOR SUPPORTING DENTAL HANDPIECES

BACKGROUND OF THE INVENTION

The present invention is directed to a device or apparatus for supporting at least one dental handpiece which apparatus includes a housing means for supporting a dental handpiece being disposed in the housing and including an annular or ring-shaped member for receiving and supporting the handpiece and means disposed adjacent the annular member for sensing the presence of the handpiece without contacting the handpiece. The output of the sensing means is utilized to actuate electrical drives when the handpiece is removed from the apparatus and to shut down or turn off the electrical drives when the handpiece is replaced in the apparatus.

It is known to provide apparatus for dental handpieces, which are provided with a switch which will be actuated when the handpiece is removed from a support portion of the apparatus and is replaced. In an example, the removal of the handpiece from the apparatus will cause a switching on of an electrical supply for the apparatus or the handpiece such as a drill drive or an electrical device associated with the handpiece such as an aspirating or suction motor of a suction removal system. The electrical switch preferably has a spring loaded actuating arm, which extends into a pocket or recess, which receives the handpiece so that when the handpiece is returned to the recess of the apparatus it causes the actuating arm of the switch to be moved. Thus, either the removal or the insertion of the handpiece into and out of the recess will cause the switch to be automatically actuated.

Since the apparatus contains several parts fitting precisely with one another, such an apparatus must be constructed with a high dimensional precision and are thus relatively costly to construct. In order to guarantee a reliable circuit, it is moreover necessary to precisely adjust the electrical switch as well as the actuating arm which passes through a support section and into the receiving recess or opening for the handpiece. The precise adjustment of the actuating arm will also include a precise adjustment of the tension or pressure of the spring. In addition, it is disadvantageous that the receiving opening or recess for the handpiece must be matched to the respective handpiece. For handpieces, which have a great deviation from one another in diameter, the known device will require a different size recess.

SUMMARY OF THE INVENTION

The present invention is directed to providing an apparatus for supporting at least one dental handpiece which apparatus is an improvement over the known apparatus, is simpler to manufacture and assemble, requires no precise adjustment of the parts effecting the circuit of the sensing means and is largely independent of particular type or structure of the handpiece to be stored therein. In particular, the principles of the present invention are directed to providing an apparatus which is provided with a simplified means for supporting and enables the apparatus to be utilized for handpieces of different types with different handpiece diameters, for example, handpieces which include turbine handpieces, electric motor handpieces and suction handpieces.

To accomplish these tasks, the present invention is directed to an apparatus for supporting at least one dental handpiece comprising a housing, means for supporting a dental handpiece being disposed in said housing and including an annular member for receiving and supporting the handpiece, and means disposed adjacent the annular member for sensing the presence of the handpiece without contacting the handpiece, said means for sensing producing signals to indicate the presence and absence of the handpiece in the annular member.

The means for sensing in a contactless fashion may include means for producing a light barrier which is broken by the depositing of a handpiece in the annular ring of the apparatus or the means may utilize a coil in a resonant circuit so that the depositing of a handpiece will effect the output of the coil and resonant circuit. Preferably, both embodiments include providing the means for sensing on a carrier member, which can be removably attached to the housing so that existing apparatuses can be selectively converted to an apparatus with the simple switching installation of the present invention or be subsequently equipped with the contactless sensing means.

DESCRIPTION OF THE PREFERRED EMBODIMENTS

Figure 1:
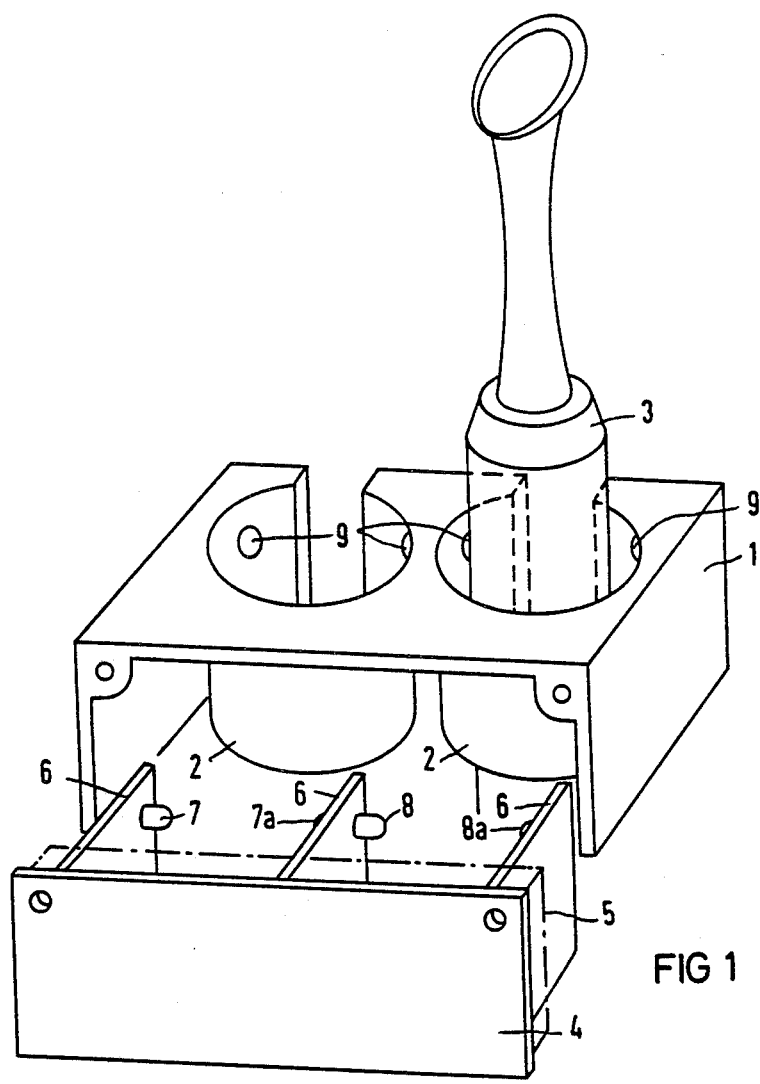
FIG. 1 is an isometric view with portions partially removed for purposes of illustration.

The principles of the present invention are particularly useful, when incorporated in an apparatus, which includes a housing 1, which has means 2 for supporting handpieces which means for supporting the handpiece includes a sleeve-shaped mounting support part or annular member 2 which has a recess for receiving the handpiece. In the sample embodiment, only one handpiece, namely a suction handpiece 3, is illustrated and preferably at its removal from the sleeve 2, a suction motor, which is associated with the handpiece, will be switched on or actuated.

The mounting support part or annular member 2 in a known fashion has an open slot or side face, which faces the operator of the device. Thus, after removal of the handpiece 3 in an axial direction from the sleeve 2, the handpiece and its supply lines can be moved laterally from the axis of the sleeve 2.

In the present instance, housing 1 is illustrated as having a rectangular shape and has a removable rear wall 4. On the removal wall 4, a plate bar 5 (shown in chain lines) is arranged to receive electrical components or electronic subassemblies for the means for sensing, which, as illustrated in FIG. 1, include means for producing a light barrier. In addition, the rear wall or carrier 4 has projection 6 which projects 5 at right angles to the wall so that they will extend into the housing 1. These members or projections 6 support diodes 7, 7a, 8 and 8a wherein the diodes 7 and 8 are light emitting diodes and the diodes 7a and 8a are the corresponding photo diodes of the means for forming a light barrier.

Since the entire apparatus and particularly the housing 1 which includes the annular sleeve like members 2 are fabricated from opaque material, apertures 9 are provided in the annular members 2. Thus, when the rear wall 4 is mounted on the housing 1, the light emitted or transmitted by diodes 7 and 8 can be received by the photodiodes or receivers 7a and 8a, respectively. When a handpiece such as 3 is present in the sleeve 2, it will block the transmission of the light between diodes 8 and 8a but when handpiece 3 is not present, the light will be transmitted between the diodes.

The rear wall 4 is constructed in the form of a part, which can be inserted into the housing 1 so that in the case of a defective electronic system or diode, an easy exchange of the component is possible. The projections 6 together with the plate bar 5 are advantageously detachably connected to the rear of wall 4, so that the components can be furnished to or subseqently added to a housing to convert an existing device without any change in the construction of the housing. Thus, the same housing can be for either a simple apparatus for supporting handpieces, which apparatus has no capabilities of switching on a device in response to removal of a handpiece or can be converted to an apparatus which does have the possibility of controlling the switching on of the device upon the removal of a handpiece.

In the embodiment illustrated in FIG. 2, the carrier plate 4, which forms a rear wall of the housing 1, is provided with carriers 12, which support induction coils 10 and 11 as part of a resonant circuit, which will be explained in greater detail with reference to FIG. 4. As a result of the approach of a handpiece such as 3 near the coil 10 as it is being placed in the recess formed by the annular member 2, the output of the coil 10 will become detuned to change its oscillation characteristic and, therefore, create a switching function in the associated electronic components. As in the previous embodiment, the rear wall 4 is constructed in the form of an insert and provides support for the electrical components or subassemblies which control the switching relays associated with each of the coils 10 and 11.

Figure 3:
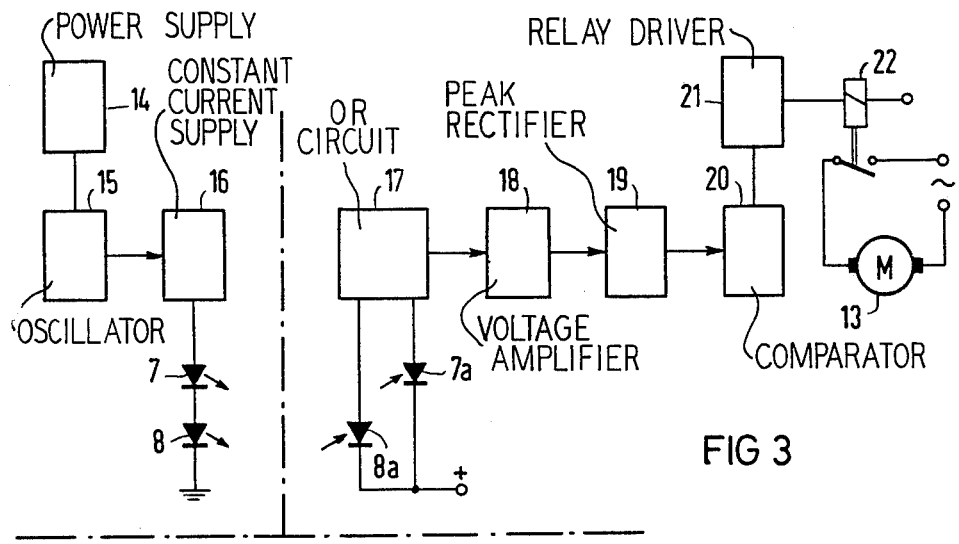
FIG. 3 is a circuit diagram of one embodiment of the invention such as illustrated in FIG. 1.

In FIG. 3 a box circuit diagram of the embodiment utilizing the means for producing a light barrier is illustrated. The diagram is illustrated as controlling a relay switch 22 for an electric drive motor 13 such as a motor used with a suction or aspirating pump, which will be switched on and off when either one of the two light barriers formed by the diodes 7 and 7a or the diodes 8 and 8a are unbroken. The light transmission side of the switching insulation which side utilizes the light emitting diodes 7 and 8, is formed by an oscillator such as an astable flip-flop 15, which is fed from a power supply such as a normal commercial current source 14. The oscillator 15 actuates a constant current source 16, which supplies the necessary current for the light emitting diodes 7 and 8, which preferably operate in the infrared range. Since the constant current source 16 supplies a load independent current for the diodes 7 and 8, several emitting diodes can be provided without the circuit requiring any changes or subsequent adjustments.

The receiving side of the light barrier is formed by an OR circuit 17, which receives a signal from either one of the photo diodes or receivers 7a or 8a. The OR circuit 17 is connected through a voltage amplifier 18, a peak rectifier 19 to a comparator 20 and then to a relay driver 21. The relay driver 21 operates the relay 22 for switching the motor 13 on and off by opening and closing contacts for the electric motor 13.

When an infrared transmission signal strikes either of the receiving diodes 7a or 8a, the output of the diodes is evaluated by the OR circuit 17 which contains several IR diodes and conveys to the AC voltage amplifier 18. The infrared signal, which is created by the infrared light, is amplified by the AC voltage amplifier 18 and is then rectified in the rectifier 19. The rectified signal is then compared to a fixed signal in a threshold value switch or comparator 20 whose output is conveyed to the relay drive 21. The infrared signal received by the diodes 7a or 8a is only received when one or more handpieces are removed from their supporting means such as annular member 2 of the apparatus. Thus, the circuit diagram will cause the motor 13 to be actuated when light is received by either the diode 7a or 8a.

Figure 2:
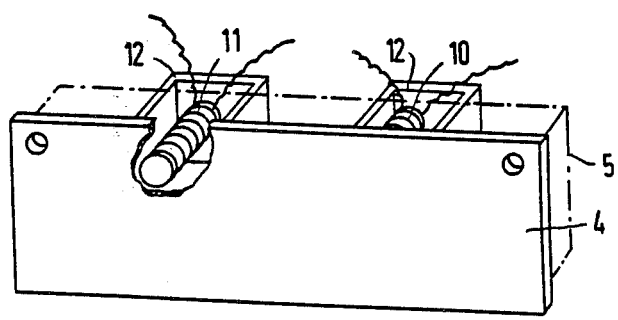
FIG. 2 is an embodiment of a portion of the carrier member of FIG. 1.
Figure 4:
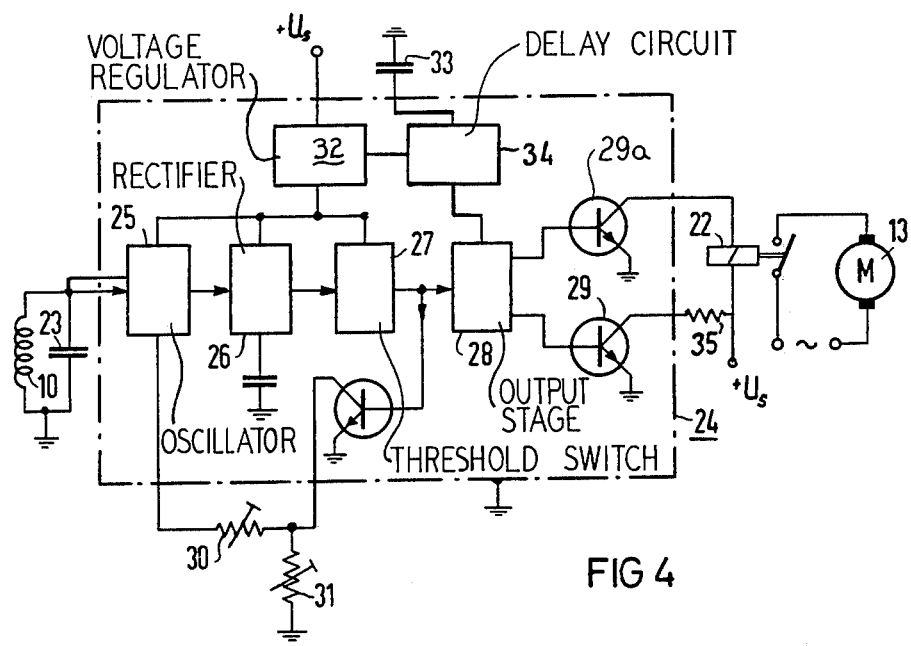
FIG. 4 is an electrical circuit diagram of a second embodiment such as illustrated in FIG. 2.

In FIG. 4, a basic circuit diagram for the embodiment illustrated in FIG. 2 is illustrated with an inductive proximity switch 24. In this embodiment, the induction coil 10 or 11, respectively, with a capacitor 23 forms a parallel resonant circuit, which is altered upon the approach of a metal part such as the depositing of a handpiece 3 consisting of metal or having metal parts in the recess of the annular member 2. The oscillation amplitude of an oscillator 25, which is arranged in the monolithic integral threshold switching stage or proximity switch 24, is also changed. The switching stage or proximity switch 24 is a commercial unit which is available under a designation of a proximity switch TCA 205A.

Briefly, the oscillation from the oscillator 25 is rectified in a rectifier 26 and the output is conveyed to a threshold switch 27. If a specific level, which is determined by the integrated circuit is not reached or met, the threshold switch 27 responds and switches over the input leads to the relay 22 via an output switch or output stage 28, which is connected to a pair of transistors 29 and 29a. One of the transistors 29 is connected to a source of power $U_s$ via a resistor 35 and the other transistor 29a is connected through the relay 22 to the same power supply. Preferably, the resistor 35 has the same resistance as the relay 22. Thus, when the output stage 28 actuates the transistor 29, which is connected through resistor 35, the relay 22 is out of the circuit and as illustrated is in an open condition. If the threshold switch 27 receives a determination of the removal of the handpiece adjacent to coil 10, the change in the output of the coil oscillation of the coil 10 will cause a switching off of the transistor 29 and a switch on of the other transistor 29a which then puts the relay 22 in the circuit to cause closing of the circuit for the motor 13.

In the circuit, variable resistance 30 and 31 are utilized with the resistance 30 changing the distance necessary for the approach to the resonant circuit formed by the coil 10 and capacitor 23 and the other adjustable resistance 31 serving the purpose of determining the hysteresis. Element 32 designates a voltage stabilizing stage for the subassembly of the proximity switch 24 and the delay time can be controlled by the capacitor 33 which acts through a delay circuit 34 so that the delay time of the pulse generator in the threshold switch 27 can be determined.

Although various minor modifications may be suggested by those skilled in the art, it should be understood that I wish to embody within the scope of the patent granted hereon all such modifications as reasonably and properly come within the scope of my contribution to the art.

I claim:

1. In an apparatus for supporting a dental handpiece comprising a structure with one end connected to a source of supply for the handpiece by a supply line, said apparatus comprising a housing, means for supporting the structure of the dental handpiece being disposed in the housing and including a support member having a cup-shaped recess for receiving and supporting each handpiece adjacent said one end, and an electrical switching installation including a switching means for controlling the flow from the source in the line to the handpiece being positioned in the region of each recess of the support member for actuation during removal and depositing of the structure of the handpiece therein, the improvements comprising said switching means including means for producing a light barrier to extend across a portion of the recess of the support member to be interrupted by the presence of the structure of the handpiece in the recess, said means for forming a light barrier including a transmitter and a receiver each operating in the infrared range, means for mounting the receiver and transmitter at a spacing approximately corresponding to the inside diameter of the recess of the support member, said means for mounting being insertable into the housing and positioning the transmitter and receiver at the recess of the support member.

2. In an apparatus according to claim 1, wherein the support member has a pair of openings in the wall forming the cup-shaped recess, said transmitter being a light emitting diode and receiver being a photo diode and said means for mounting the receiver and transmitter positioning the transmitter and receiver at the openings in the wall of the cup-shaped recess of the support member.

3. In an apparatus according to claim 1, wherein the means for mounting has a wall portion forming a rear wall of the housing of the device of the apparatus.

4. In an apparatus according to claim 1, wherein the electrical circuit for operating the transmitter and the receiver are mounted on a carrier forming part of the means for mounting the transmitter and receiver.

5. In an apparatus according to claim 1, wherein the housing of the apparatus contains means for supporting a plurality of dental handpieces with an annular support member for each handpiece, said means for forming a light barrier having a separate receiver and transmitter for each of the annular support members being mounted on a common carrier for the means for mounting the receiver and transmitter.

6. In an apparatus for supporting a dental handpiece comprising a structure with one end being connected to a source of supply for the handpiece by a supply line, said apparatus comprising a housing, means for supporting the structure of the dental handpiece being disposed in the housing and including a support member having a cup-shaped recess for receiving and supporting the one end of the structure of the handpiece and an electrical switching installation including a switching means for controlling the flow from the source in the line to the handpiece being positioned in the region of the recess of the support member for actuation during removal and depositing of a handpiece therein, the improvements comprising said switching means including a coil of an inductive resonant circuit, means for mounting the coil including a part inserted into the housing to position the coil adjacent the recess of the support member, and said structure of the handpiece including a material which will mistune the resonant circuit as a handpiece approaches the coil by being inserted in the recess.

7. In an apparatus according to claim 6, wherein the electrical switching installation includes a proximity switch having an input connected to a resonant circuit, said proximity switch being in the form of an integrated component.

8. In an apparatus according to claim 6, wherein the means for mounting the coil has a wall portion forming the rear wall of the housing.

9. In an apparatus according to claim 6, wherein the electrical circuit for operating the coil of the inductive resonant circuit are mounted in the carrier forming part of the means for mounting the coil of the inductive resonant circuit.

10. In an apparatus according to claim 6, wherein the housing contains means for supporting a plurality of dental handpieces with an annular support member for each handpiece, said switching means including a coil of an inductive resonant circuit for each annular support member being mounted on a common carrier for the means for mounting the coil.

* * * * *